(12) United States Patent
Yagi et al.

(10) Patent No.: US 7,721,898 B2
(45) Date of Patent: May 25, 2010

(54) COATING MATERIAL FOR LEUKOCYTE REMOVAL FILTER AND THE FILTER

(75) Inventors: Yasuhiko Yagi, Chiba (JP); Hirofumi Miura, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 598 days.

(21) Appl. No.: 10/485,554

(22) PCT Filed: Jul. 24, 2002

(86) PCT No.: PCT/JP02/07502

§ 371 (c)(1),
(2), (4) Date: Aug. 11, 2004

(87) PCT Pub. No.: WO03/011924

PCT Pub. Date: Feb. 13, 2003

(65) Prior Publication Data

US 2004/0253204 A1 Dec. 16, 2004

(30) Foreign Application Priority Data

Jul. 31, 2001 (JP) ............................. 2001-230737
Jul. 31, 2001 (JP) ............................. 2001-230738

(51) Int. Cl.
*B01D 71/06* (2006.01)
(52) U.S. Cl. ........................... 210/500.35; 210/500.42; 210/502.1; 210/503; 210/505
(58) Field of Classification Search ................ 210/490, 210/502.1, 503–508, 645, 650, 654, 767, 210/500.27, 500.35, 500.42; 530/412–417; 428/364, 375; 526/303.1, 319–325, 328.5; 424/78.08, 78.31
See application file for complete search history.

(56) References Cited

U.S. PATENT DOCUMENTS

| 4,936,998 | A | * | 6/1990 | Nishimura et al. ........... 210/638 |
| 5,030,684 | A | * | 7/1991 | Rauch-Puntigam et al. . 524/513 |
| 5,244,578 | A | * | 9/1993 | Ohnishi et al. ............... 210/650 |
| 5,282,971 | A | * | 2/1994 | Degen et al. ................. 210/645 |
| 5,371,147 | A | * | 12/1994 | Spinelli et al. ............... 525/288 |
| 5,407,581 | A | * | 4/1995 | Onodera et al. ............. 210/654 |
| 6,113,785 | A | * | 9/2000 | Miura et al. ........... 210/500.41 |
| 6,267,898 | B1 | | 7/2001 | Fukuda et al. |
| 6,361,826 | B2 | * | 3/2002 | Olson et al. ................. 427/189 |

FOREIGN PATENT DOCUMENTS

| EP | 0 561 379 | 9/1993 |
| EP | 0 606 646 | 7/1994 |
| EP | 0 869 138 | 10/1998 |
| EP | 1 016 426 | 7/2000 |
| JP | 60-141705 | 7/1985 |
| JP | 2001-300221 | 10/2001 |
| WO | WO99/11304 | 3/1999 |

* cited by examiner

*Primary Examiner*—Joseph W Drodge
(74) *Attorney, Agent, or Firm*—Young & Thompson

(57) ABSTRACT

It is intended to provide a polymer for coating a leukocyte removal filter material which is excellent in the capability of removing leukocytes. It is further intended to provide a filter whereby both of leukocytes and platelets can be highly efficiently removed from a blood product containing leukocytes and platelets. The above objects can be achieved by using a polymer for coating a leukocyte removal filter material which comprises a unit originating in a hydrophobic polymerizable monomer, a unit originating in a polymerizable monomer containing a basic nitrogen-containing part, and a unit originating in a polymerizable monomer containing a protonic neutral hydrophilic part.

7 Claims, No Drawings

US 7,721,898 B2

COATING MATERIAL FOR LEUKOCYTE REMOVAL FILTER AND THE FILTER

TECHNICAL FIELD

The present invention relates to a polymer for coating a leukocyte removal filter material and to a leukocyte removal filter having this novel polymer on the surface. In particular, the present invention relates to a polymer suitable for coating a filter used for removing leukocytes that cause side effects during blood transfusion from blood products for transfusion at high efficiency, and to a leukocyte removal filter having this novel polymer on the surface. The present invention also relates to a filter capable of removing leukocytes and platelets causing side effects during blood transfusion at the same time and at high efficiency.

BACKGROUND ART

In recent years, leukocyte-free blood transfusion in which leukocytes contained in a blood product are removed in advance is increasingly applied in the field of blood transfusion. This is due to the finding that the side effects such as headache, nausea, chills, and an anhemolytic exothermic reaction, as well as heavy side effects such as alloantigen sensitization, post-blood transfusion graft versus host disease (GVHD), and virus infection are mainly induced by leukocytes contained in blood products used for the blood transfusion.

Methods for removing leukocytes from blood products are broadly classified into a centrifuge separation method, making use of differences in the specific gravity of blood components, and a filter method using a fiber material or a porous material having continuous pores as a filter material. The filter method is more popular due to higher leukocyte removing capability, simple procedure, lower cost, and the like.

Increasing recognition on the importance of blood transfusion using a leukocyte-free blood product in recent years has encouraged a desire for a leukocyte removal filter possessing more excellent leukocyte removing capability that can prevent the above-mentioned heavy side effects.

Since platelets are known to produce antiplatelet antibodies when blood transfusion is frequently conducted, development of the technology for removing platelets has also been desired to suppress production of antiplatelet antibodies. Conventionally, an effort of simultaneously removing leukocytes and platelets has been undertaken by decreasing the pore diameter of the filter, for example, by narrowing the space between fibers in the filter material so that platelets can be captured. However, decreasing the filter pore size results in a slow filtering speed, requiring a long time for removing leukocytes and platelets. Therefore, a technology for removing platelets at high efficiency at the time of removing leukocytes by a means other than decreasing the filter pore size has been desired.

To improve the leukocyte removal capability of a leukocyte removal filter, both physical factors and chemical factors of the filter must be taken into consideration.

The physical factors relate to the physical structure of the filter material such as a specific surface area, fiber diameter, void ratio, bulk density, and thickness in the case of fibrous media such as a nonwoven fabric, and a pore size, porosity, and thickness in the case of porous materials containing continuous pores. The physical factors of filter materials are commonly known to greatly contribute to the leukocyte removal capability of a filter. It is also known that the leukocyte removal capability can be improved by using a material with a high specific surface area, specifically by using superfine fibers having a small fiber diameter, increasing a filling density, or decreasing a pore size.

The chemical factors, on the other hand, relate to denaturing or processing a filter material surface by, for example, causing a polymer to attach to the surface to increase the affinity with leukocytes or to improve wettability. In general, when blood is caused to come into contact with various polymers, blood acts differently according to the properties of the surface of the materials in terms of occurrence or nonoccurrence of blood clotting or cell activation. Although the reason for the above-described difference is still to be clarified, complicated mutual actions of the cells in blood with the material surface are thought to be one of the reasons ("Polymeric Materials For Medical Use" edited by Biomedical Polymer Material Editing Committee, 1981, Center for Academic Publications Japan).

If the denatured or processed surface of the material is viewed in terms of the hydrophilic or hydrophobic properties, a polymeric material with a hydrophilic surface exhibits only small surface energy with blood and small mutual interactions with proteins or blood cells, in general. For this reason, the polymeric material with a hydrophilic surface is reported to have a tendency of suppressing blood clotting and morphological change in blood cell ("Biomaterial Science" 2nd series, 135, 1982, Nankodo Co., Ltd.). Therefore, hydrophilic modification of the filter material used for blood processing is effective. Introducing hydrophilic monomers or polymers by graft polymerization or coating to the surface of the filter material is known as a technique known in the art.

WO 87/05812 (Japanese Patent Publication No. 6-51060) discloses a filter containing a nonionic hydrophilic group and a basic nitrogen-containing functional group on the surface and having a basic nitrogen atom content of 0.2-4.0 wt % in the circumferential surface area, and describes that the filter can efficiently remove leukocytes with only a slight amount of platelet loss. The patent specification also describes that the filter has leukocyte removal performance more excellent in comparison with conventional filters without coating (for example, Japanese Patent Publication No. 2-13587). EP 0606646 (KR 129767 and Japanese Patent Application Laid-open No. 6-246862) discloses a filter having leukocyte removal performance. The filter contains basic functional groups and nonionic hydrophilic groups on the surface at a molar ratio of the basic functional groups to the nonionic hydrophilic groups of 0.6-6 and has a density of the basic functional groups of $5\times10^{-5}$ to 0.1 meq/m$^2$.

However, if positively charged functional groups such as a dimethylamino group, diethylamino group, and quarternary ammonium salt are introduced at a high density together with nonionic hydrophilic groups onto the surface of a material, cells in blood products, in particular erythrocytes, are firstly adsorbed in the material on the surface and occupy the seats for leukocytes to be adsorbed, resulting in a tendency of preventing improvement in the leukocyte removal capability. In this manner, the conventional technique of surface modification with positively charged functional groups provides only a small effect on the selectivity in the adsorption of leukocytes and erythrocytes and has difficulty in providing the filter with high leukocyte removal capability. If the density of the positively charged functional groups is increased with an objective of increasing platelet removal capability, platelets may be undesirably activated inducing morphological change and the like. Such a material cannot be used as the coating material of the filter for simultaneous removal of leukocytes and platelets.

WO 89/03717 (Published Japanese Translation of PCT Application No. 3-502094) discloses a filter using a porous web with a critical wetting surface tension (CWST) of 53-90 dyn/cm produced by grafting 2-hydroxyethyl methacrylate (HEMA) with methyl acrylate (MA) or methyl methacrylate (MMA) and changing their proportion. This filter, however, is not suitable for efficiently removing platelets.

As an invention relating to a technology for efficiently removing not only leukocytes but also platelets, Japanese Patent Application Laid-open No. 2000-197814 discloses a hydrophilic coating material containing quaternary ammonium salt. However, leukocyte removal capability and platelet removal capability of these filters are not necessarily sufficient. Although the use of a quaternary ammonium salt remarkably promoted hydrophilic properties and the CWST of the filter technically exceeded the level achieved by WO 89/03717 (Published Japanese Translation of PCT Application No. 3-502094), the method requires a washing step after the coating step to reduce elution.

As an invention to remove not only leukocytes but also platelets efficiently, U.S. Pat. No. 5,498,336 (EP 500472, Japanese Patent No. 3124565, Japanese Patent Application Laid-open No. 6-142196, and Japanese Patent No. 3273061) discloses a porous filter material with a positive surface zeta potential comprising a substance having a cationic functional group such as an amino group incorporated in or bonded to the material and a means for avoiding clogging of the filter with leukocytes and platelets by providing the main filter on the blood outlet side with a plus zeta potential of the porous filter material and the main filter on the blood inlet side with a minus zeta potential. If the zeta potential is increased to increase the leukocyte adsorption capability, not only leukocytes and platelets are adsorbed, but also erythrocytes are adsorbed, resulting in a general tendency of an increase in the process pressure. The leukocyte removal capability of the filter declines with time. As a countermeasure against the pressure increase of the filter, a main filter having a negative zeta potential is provided as an upper layer with an objective of suppressing adsorption of leukocytes and platelets in the upper layer. Although this method can suppress the pressure and reduce leakage of leukocytes throughout the entire process time, the leukocyte removal capability and platelet removal capability are not yet sufficient.

Japanese Patent Application Laid-open No. 7-25776 discloses a filter material with less elution that can selectively remove leukocytes while maintaining high platelet permeability and high leukocyte removal capability, wherein the surface of the filter material is coated with a polymer having both a hydrophobic part and a polyethylene oxide chain. The patent specification presents polymerizable monomers having hydrophobic parts and a polymer for coating for leukocyte removal containing polyethylene oxide chains and basic nitrogen-containing functional groups. The hydrophobic parts are introduced to decrease elution, whereas the polyethylene oxide chains are introduced to increase permeability of platelets. The objectives differ from that of the objective of ensuring high leukocyte removal capability and high platelet removal capability at the same time in the present invention.

DISCLOSURE OF THE INVENTION

An object of the present invention is to provide a coating material, for a leukocyte removal filter exhibiting excellent leukocyte removal capability per unit area when leukocytes are removed from a blood product containing leukocytes. Another object of the present invention is to provide a filter for leukocyte removal using the polymer, the filter requiring only a small volume for a filter apparatus, by which a loss of useful components remaining in the filter can be reduced, and being free from a pressure rise at a fixed flow rate as well as from extension of process time during the head drop processing due to erythrocyte adsorption. Still another object of the present invention is to provide a filter capable of simultaneously removing leukocytes and platelets at high efficiency from a blood product containing the leukocytes and platelets.

Based on the assumption that a polymer for coating a filter material and the filter exhibiting remarkably excellent leukocyte removal performance can be obtained if mutual action with erythrocytes can be suppressed while maintaining a high leukocyte affinity, the inventors of the present invention have conducted extensive studies to develop a polymer for coating a leukocyte removal filter material and the filter. As a result, the inventors have found that a polymer for coating a leukocyte removal filter material formed from a unit originating from a hydrophobic polymerizable monomer, a unit originating from a polymerizable monomer containing a basic nitrogen-containing part, and a unit originating from a polymerizable monomer containing a protonic neutral hydrophilic part exhibits an action of suppressing a mutual action with erythrocytes while maintaining high leukocyte affinity. This finding has led to the completion of the present invention. The present inventors have further found that a filter for leukocyte removal that absorbs only an extremely small amount of erythrocytes and can selectively absorb leukocytes at a high density by causing this polymer to be present on the surface of the filter material can be provided. This finding also has led to the completion of the present invention.

Even in the case where products, such as a whole blood product, an erythrocyte product from which platelet-rich plasma has been removed, and an erythrocyte product from which platelet-poor plasma and buffy coat layers have been removed (these products may be hereinafter referred to collectively as "products" from time to time), are processed, the above filter can exhibit high leukocyte removal capability, while allowing downsizing of the filter apparatus, enabling a loss of useful components remaining in the filter to be reduced, and being free from a pressure rise at a fixed flow rate as well as from extension of process time during the head drop processing due to erythrocyte adsorption.

Furthermore, the present inventors have conducted extensive studies to develop a leukocyte and platelet removal filter highly excelling in leukocyte and platelet capability. As a result, the inventors have found that a filter containing a polymer formed from a unit originating from a hydrophobic polymerizable monomer, a unit originating from a polymerizable monomer containing a basic nitrogen-containing functional group part, and a unit originating from a polymerizable monomer containing a protonic neutral hydrophilic part, and each unit of the polymer being on the surface of the filter material at a specific proportion and in a specific amount on the surface can achieve the above object.

Moreover, the present inventors have found that the filter can exhibit high leukocyte removal capability and high platelet removal capability when a whole blood product is processed and can also exhibit high leukocyte removal capability when a product, such as an erythrocyte product from which platelet-rich plasma has been removed or an erythrocyte product from which plasma and buffy coat layers have been removed, is processed. These findings have led to the completion of the present invention.

Therefore, the present invention relates to:

Claim 11. A filter for removing leukocytes and platelets, said filter having a polymer consisting of:

5-45 mol % of a unit originating from a hydrophobic polymerizable monomer selected from the group consisting of: methyl acrylate, methyl methacrylate, ethyl acrylate, ethyl methacrylate, butyl acrylate, butyl methacrylate, phenyl acrylate, phenyl methacrylate, ethylhexyl acrylate, ethylhexyl methacrylate, trichloroethyl acrylate, and trichloroethyl methacrylate;

1-15 mol % of a unit originating from a polymerizable monomer containing a basic nitrogen-containing part, wherein said polymerizable monomer is selected from the group consisting of: dimethylaminoethyl acrylate, dimethylaminoethyl methacrylate, diethylaminoethyl acrylate, diethylaminoethyl methacrylate, 3-dimethylamino-2-hydroxypropyl acrylate, and 3-dimethylamino-2-hydroxy propyl methacrylate; and the balance of a unit originating from a polymerizable monomer containing a protonic neutral hydrophilic part, wherein said polymerizable monomer is 2-hydroxyethyl methacrylate or hydroxypropyl methacrylate, wherein the filter has an average pore diameter of 1-60 um, and said polymer is present on the entire surface of the filter in an amount of 5-50 mg/m$^2$ per unit area of the filter surface.

Claim 12. The filter for removing leukocytes and platelets according to claim 11, wherein the polymer is a vinyl polymer.

Claim 14. The filter for removing leukocytes and platelets according to claim 11, wherein the basic nitrogen-containing part is a tertiary amino group.

Claim 15. The filter for removing leukocytes and platelets according to claim 11, wherein the protonic neutral hydrophilic part is a hydroxyl group.

Claim 16. The filter for removing leukocytes and platelets according to claim 11, wherein the filter material is a fibrous medium or a sponge-like structural material.

Claim 17. The filter for removing leukocytes and platelets according to claim 16, wherein the filter material is a non-woven fabric.

Claim 18. The filter for removing leukocytes and platelets according to claim 16, wherein, the filter material has a specific surface area of 1.0 m2/g or more and a void ratio of 70% or more, the average fiber diameter is 0.3-3.0 um, and the filling density is 0.1-0.5 g/cm$^3$.

BEST MODE FOR CARRYING OUT THE INVENTION

The term "polymer" in the present invention means a polymer for coating a leukocyte removal filter material formed from a unit originating from a hydrophobic polymerizable monomer, a unit originating from a polymerizable monomer containing a basic nitrogen-containing part, and a unit originating from a polymerizable monomer containing a protonic neutral hydrophilic part.

The term "hydrophobic polymerizable monomer" in the present invention means a polymerizable monomer having extremely low affinity with water and containing neither a basic nitrogen-containing part nor a protonic neutral hydrophilic part in the molecule.

The term "unit" in the present invention means a minimum repeating unit originating from each polymerizable monomer in a polymer molecule. For example, in the case of the addition polymerization of a polymerizable monomer of vinyl compound with the formula $CH_2=CXY$ (wherein X is H or a substituent other than H and Y is a substituent other than X) by simply opening the double bond, the minimum repeating unit is $-(CH_2-CXY)-$. In the case where the polymer is synthesized by polycondensation from a polymer precursor of the formula A-(R)—B, (wherein R indicates a part not releasable by polymerization and A and B are releasable parts during the polymerization reaction), —(R)— can be given as the minimum repeating unit of the polymer released A and B.

The term "hydrophobic monomer" in the present invention means a polymerizable monomer having water solubility of 12 (g/100 g of water) or less at 20° C. If the solubility is more than 12 (g/100 g of water), the high leukocyte removal capability available in the present invention may not be undesirably obtained. More preferable solubility is 2 (g/100 g of water) or less.

The solubility can be determined by a known method, such as a dew point method, thermal analysis, electric method comprising measuring the electromotive force or electric conductivity of the solution, gas chromatography analysis, and tracer method, in the case where the polymerizable monomer is a solid. In the case where the polymerizable monomer is a liquid, the solubility can be determined by the same methods as applied to a solid polymerizable monomer, in addition by a known method, such as a capacitance method, light scattering method, vapor pressure method, or the like, all of which are known in the art. As a simpler method, when the polymerizable monomer has a boiling point sufficiently higher than the boiling point of water, a method of vaporizing water from a saturated aqueous solution of the polymerizable monomer and measuring the weight of the residue can be used.

As examples of the hydrophobic polymerizable monomer, styrene, methylstyrene; acrylates or methacrylates such as methyl acrylate, methyl methacrylate, ethyl acrylate, ethyl methacrylate, butyl acrylate, butyl methacrylate, phenyl acrylate, phenyl methacrylate, ethylhexyl acrylate, ethylhexyl methacrylate, trichloroethyl acrylate, and trichloroethyl methacrylate; alkenes such as pentene, hexene, heptene, and octene; organosilicon compounds such as silicone, siloxane; and an organic fluorine polymerizable monomer with one or more fluorine atoms substituting for hydrogen atoms on ethylene can be given from the viewpoint of easiness in availability and handling. However, the hydrophobic polymerizable monomer is not limited to those compounds as described above. Of these, from the viewpoint of easy availability, easy handling, and the like, monomers having a vinyl group as a polymerizable part that can produce a vinyl polymer by addition polymerization (vinyl polymerization) are preferable. Moreover, preferable hydrophobic polymerizable monomers are acrylic acid derivatives and methacrylic acid derivatives. Acrylates and methacrylates are most preferable hydrophobic polymerizable monomers.

Materials having a basic nitrogen-containing functional group are reported to produce positive charges on the surface in a physiological fluid and cause leukocytes having negative charges to be adhered.

A primary amino group, secondary amino group, tertiary amino group, quaternary amino group, and nitrogen-containing aromatic groups such as a pyridyl group and imidazole group can be given as a basic nitrogen-containing functional group, for example. A tertiary amino group is particularly preferable as a basic nitrogen-containing part.

As examples of the polymerizable monomer having a basic nitrogen-containing part, vinyl derivatives of nitrogen-containing aromatic ring compounds such as vinyl amine, 2-vinylpyridine, 4-vinylpyridine, 2-methyl-5-vinylpyridine, 4-vinylimidazole, N-vinyl-2-ethylimidazole, and N-vinyl-2-methylimidazole; acrylates and methacrylates such as dimethylaminoethyl acrylate, dimethylaminoethyl methacrylate, diethylaminoethyl acrylate, diethylaminoethyl methacrylate, 3-dimethylamino-2-hydroxypropyl acrylate and 3-dimethylamino-2-hydroxy propyl methacrylate; acrylic acid amide and methacrylic acid amide derivatives such as N,N-dimethylaminoethyl acrylic acid amide, N,N-dimethylaminoethyl methacrylic acid amide, N,N-diethylaminoethyl acrylic acid amide, N,N-diethylaminoethyl methacrylic acid amide, and N,N-dimethylaminopropyl acrylic acid amide; styrene derivatives such as p-dimethylaminomethylstyrene and p-diethylaminoethylstyrene; and derivatives of quaternary ammonium salt produced by reacting these polymerizable monomers with an alkyl halide can be given from the viewpoint of easiness in availability and handling. The polymerizable monomer having a basic nitrogen-containing part, however, are not limited to these monomers. Of these, from the viewpoint of easy availability, handling easiness, and the like, monomers having a vinyl group as a polymerizable part that can produce a vinyl polymer by addition polymerization (vinyl polymerization) are preferable. As polymerizable monomers containing a basic nitrogen-containing part, acrylic acid derivatives and methacrylic acid derivatives are preferable. Particularly preferable polymerizable monomers containing a basic nitrogen-containing part are acrylates and methacrylates. Of these, dimethylaminoethyl acrylate, dimethylaminoethyl methacrylate, diethylaminoethyl acrylate, and diethylaminoethyl methacrylate are particularly preferable.

The protonic neutral hydrophilic part is an essential part in the polymer mainly for securing wettability of the filter with blood products when the blood products are processed, in particular, for modifying the properties of the filter material surface to ensure smooth "priming" that is a procedure of causing the filter material to be saturated with the blood product at the initial stage of processing.

A monomer having a protonic neutral hydrophilic part is a monomer of which the non-polymerizable part dissociates to release protons ($H^+$). Such a monomer does not exhibit extreme acidity or extreme basicity as a carboxylic acid or a basic amino group. The term "protonic" as used in the present invention means the properties described, for example, in "Organic Chemistry, fourth edition by Morrison and Boyd (Tokyo Kagaku Dozin Co., Ltd., 1985), page 46, 1. Structure and Properties, 1.22 Solubility". The term "neutral" means properties of a compound that does not exhibit extreme acidity or extreme basicity as a carboxylic acid or a basic amino group. A monomer having a protonic neutral hydrophilic part exhibits higher hydrophilic properties as compared with a monomer having a non-protonic neutral hydrophilic part and excels in blood priming properties and blood channeling preventive properties. As the protonic neutral hydrophilic part, a hydroxyl group, an aldehyde group having a proton at the α-position, an amide group having a proton at the α-position, 1,3-dicarbonyl group, and the like can be given. As a non-polymerizable protonic neutral hydrophilic part, a hydroxyl group is particularly preferable.

Examples of the polymerizable monomer containing a protonic neutral hydrophilic part include, but are not limited to, 2-hydroxyethyl methacrylate, hydroxypropyl methacrylate, acrylamide, and methacrylamide. Of these, from the viewpoint of easy availability, handling easiness, and the like, monomers having a vinyl group as a polymerizable part that can produce a vinyl polymer by addition polymerization (vinyl polymerization) are preferable. As polymerizable monomers containing a protonic neutral hydrophilic part, acrylic acid derivatives and methacrylic acid derivatives are preferable. Acrylates and methacrylates are the most preferable polymerizable monomers containing a protonic neutral hydrophilic part.

The term "vinyl polymer" in the present invention means a vinyl polymer in a broad sense having non-cyclic main chain. Specific examples include α-substituted polyacrylic acid and derivatives thereof, polyvinyl ether, polyvinyl alcohol, polyvinyl ester, polystyrene, and their derivatives, as well as copolymers including these polymers as described in J. Brandrup; E. H. Immergut. 1989, "Polymer Handbook Third Edition" A Willey-Interscience Publication, pp. VII-5 to VII-18.

To ensure high leukocyte removing capability, said monomer composition (in terms of mol %) forming the polymer is preferably 3-50 mol % of hydrophobic polymerizable monomers, 1-40 mol % of polymerizable monomers containing a basic nitrogen-containing part, and the balance (in mol %) of the polymerizable monomer containing a protonic neutral hydrophilic part.

If the amount of hydrophobic polymerizable monomers in the polymer is less than 3 mol % or more than 50% or the amount of the polymerizable monomers containing a basic nitrogen-containing part is less than 1% or more than 40 mol %, undesirably, the leukocyte removal capability may not be improved, wettability may be impaired, or hemolysis may occur.

To ensure higher leukocyte removing capability (for which the performance must be evaluated under the over-loaded blood processing conditions), the monomer composition (in terms of mol %) forming the polymer is preferably 5-45 mol % of hydrophobic polymerizable monomers, 1-15 mol % of polymerizable monomers containing a basic nitrogen-containing part, and the balance (in mol %) of the polymerizable monomer containing a protonic neutral hydrophilic part.

A particularly preferable monomer composition in a copolymer is 10-40 mol % of hydrophobic polymerizable monomers, 1-15 mol % of polymerizable monomers containing a basic nitrogen-containing part, and the balance of polymerizable monomers containing a protonic neutral hydrophilic part.

In specifying the preferable monomer composition or the particularly preferable monomer composition in the polymer of the present invention, leukocytes and platelets removing capability was evaluated under the overloaded conditions rather than normal blood processing conditions. Consequently, a preferable range in the present invention is the range in which leukocytes and/or platelets removing capability of a certain level can be satisfied even under overloaded conditions. Since the overloaded processing conditions are severer than the normal processing conditions, polymers or filters that do not meet a certain required level under the overloaded processing conditions may often satisfy that level under the normal processing conditions. Such polymers or filters are also included in the scope of the present invention.

The monomer composition in the polymers can be determined according to a common physicochemical technique. Examples of the physicochemical technique for determining the copolymer compositions include known methods, such as the nuclear magnetic resonance spectrum method (NMR, —$^1H$, —$^{13}C$) and the pyrolysis GC/MS method, and the monomer composition can be determined using these methods. Whether or not the polymerization is carried out in accord with the charged monomer composition or there are lot-to-lot variation can also be confirmed. It is also possible to dissolve and extract the polymer coated on the surface of a leukocyte and platelet removal filter material by using a solvent for the polymer and to analyze the monomer composition in the extracted polymer in the same manner as described above. It is also possible to apply a method of dissolving the filter material for removing leukocytes and platelets and the polymer present on the surface in a deuteration solvent and determining the composition by nuclear magnetic resonance spectrum method (NMR, —$^1$H, —$^{13}$C) as a method to determine the copolymer composition.

The molecular weight of the polymer can be measured by the known gel permeation chromatography. The weight average molecular weight (Mw) is in the range of preferably 50,000-3,000,000, more preferably 100,000-2,000,000, and most preferably 200,000-1,500,000. If the weight average molecular weight (Mw) is less than 50,000, elution into the blood product may occur during a leukocyte removal process using a blood product containing leukocytes. If the weight average molecular weight (Mw) is more than 3,000,000, solubility of the polymer in the solvent used for coating decreases. In addition, there may be the case where the polymer cannot be produced in a stable manner when polymerizing.

The polymer may be either a random copolymer or a block copolymer. The random polymer is, however, more preferable since the block copolymer may have a tendency of decreasing the solubility in a solvent when used for coating and may have a tendency of impairing uniformity of coat due to micelle formation in the solution. The polymer may be usable either a linear polymer or a branched polymer. The linear polymer is, however, more preferable since the branched polymer may have a tendency of decreasing the solubility in a solvent when used for coating and may have a tendency of impairing coating uniformity due to micelle formation in the solution.

A common polymerization method can be employed for synthesizing the polymer. Addition polymerization (vinyl polymerization) and the like included in chain reaction; isomerization polymerization; and elimination reaction, polyaddition, polycondensation, addition polycondensation, and the like included in consecutive reaction may be employed.

Radicals, ions, and the like can be used as chain carriers in producing the polymer.

As the type of polymerization, solution polymerization, mass polymerization, deposition polymerization, emulsion polymerization, and the like can be given. Of these, the solution polymerization is preferable.

An example of the polymerization method is given below.

An ethanol solution in which monomers and a diazo initiator are dissolved is added dropwise to ethanol used as a polymerization solvent while stirring at a constant temperature below the boiling point of ethanol in a nitrogen atmosphere and reacted. A stabilizer and the like may be added as appropriate. The reaction yield is measured and confirmed by using a known method such as gas chromatography.

The reaction mixture may be purified by a common chemical purification method to remove impurities such as low molecular weight components and the unreacted materials which are contained in the polymer or the reaction solution containing the polymer, which may be eluted during processing of blood products. As the purification method, a method comprising pouring the reaction mixture in a solvent that dissolves the impurities, but does not dissolve the polymer, to cause the impurities to precipitate, and separating the precipitate by filtration, decantation, or the like can be given. Alternatively, a method that as required, the precipitate is washed with a solvent with solubility slightly higher than that of the precipitation solvent (a mixture of the precipitation solvent and the solvent, for example) and the precipitate is dried under reduced pressure until the weight of the precipitate becomes constant to obtain as a solid polymer can be given.

There are no specific limitations to the type of leukocyte removing filter material inasmuch as the material has pores through which the blood can be filtered. Among the various conformations of the material that can be used, fibrous media such as natural fibers, glass fibers, knit, fabric, nonwoven fabric, porous membrane, and a sponge-like structural material having a three-dimensional network of continuous pores are particularly preferable. Various materials such as organic polymer materials, inorganic polymer materials, and metals can be used without any specific limitations so long as blood cells are not easily impaired. Among these, the organic polymer materials are preferable materials due to their excellent processability such as cutting. Examples of the filter materials that can be used in the present invention include, but are not limited to, polyester, polyolefin, polyacrylonitrile, polyamide, polystyrene, polymethyl methacrylate, polyvinyl fluoride, polyurethane, polyvinyl alcohol, polyvinyl acetal, polysulfone, polyvinylidene fluoride, polytrifluorochlorovinyl, vinylidene fluoride-tetrafluoroethylene copolymer, polyether sulfone, polyacrylate, butadiene-acrylonitrile copolymer, polyether-polyamide block copolymer, ethylene-vinyl alcohol copolymer, cellulose, and cellulose acetate. Of these, polyester and polyolefin are preferable, with a particularly preferable organic filter material being polyester.

The physical structure of the filter material is known to greatly contribute to removing leukocytes. To improve the leukocyte removal capability, selection of the filter material is also an important factor.

The specific surface area as a physical structure of the filter material is $1.0\,m^2/g$ or more, and preferably $1.4\,m^2/g$ or more. In processing a blood product using a blood filter in practice, two or more filter materials with a different specific surface area are preferably arranged in such a manner that the specific surface area of the filter materials increases toward the outlet port side.

The void ratio as another factor for the physical structure of the filter material is preferably 70% or more, and particularly preferably 80% or more.

Specifically, when using a fibrous medium such as a nonwoven fabric as the filter material, the average fiber diameter is 0.3-3.0 μm, preferably 0.5-2.5 μm, and more preferably 1-2 μm. In processing a blood product using a blood filter in practice, two or more filter materials with a different average fiber diameter are preferably arranged so that the average fiber diameter of the filter materials decreases toward the outlet port side. In processing a blood product using a blood filter in practice, a prefilter with an average fiber diameter of 10-40 μm may be arranged on the inlet port side of the filter with a major objective of removing fine aggregates.

The average pore diameter is 1-60 μm, preferably 1-30 μm, and more preferably 1-20 μm. In processing a blood product using a blood filter in practice, two or more filter materials with a different average pore diameter are arranged so that the average pore diameter of the filter materials decreases toward the outlet port side. In processing a blood product using a blood filter in practice, a prefilter with an average pore diameter of 50-200 μm may be optionally arranged on the inlet port side of the filter with a major objective of removing fine aggregates. In processing a blood product using a blood filter in practice, a post-filter with an average pore diameter of 50-200 μm may be optionally arranged on the outlet port side of the filter with a major objective of preventing a distortion flow.

When the fibrous medium is filled in a container for removing leukocytes, the filling density is preferably $0.1$-$0.5\,g/cm^3$, and more preferably $0.1$-$0.3\,g/cm^3$. A method of measuring the filling density will be described by way of an example. A nonwoven fabric to be filled in is cut into pieces with a filling size ($cm^2$) and that weight (g) is measured. The density can be determined from the distance (cm) of the material compressed in the actual container.

If the specific surface area of the filter material is less than 1.0 m$^2$/g, it is difficult to remove leukocytes at a high efficiency and it is difficult to downsize the apparatus.

If the void ratio of the filter is less than 70%, the filtration rate of blood and the like is retarded, requiring a longer time for removing leukocytes and platelets.

If the average fiber diameter is less than 0.3 μm, the average pore diameter is less than 1 μm, or the filling density is more than 0.5 g/cm$^3$, the filter may be clogged with blood cells or the pressure loss may be increased. If the average fiber diameter is more than 3.0 μm, the average pore diameter is more than 60 μm, or the filling density is less than 0.1 g/cm$^3$, the leukocyte removal capability may be decreased.

A porous membrane or a sponge-like structural material having a three-dimensional network of continuous pores used as a filter material preferably has an average pore diameter of 1-60 μm. If the average pore diameter is less than 1 μm, the filter may be clogged with blood cells or the pressure loss may be increased. If the average pore diameter is more than 60 μm, the leukocyte removal capability declines.

To ensure higher leukocyte removal capability and higher platelet removal capability at the same time, the filter contain the above polymer on at least a part of the surface of the filter material, a polymer comprising 5-45 mol % of a unit originating from a hydrophobic monomer, 1-15 mol % of a unit originating from a polymerizable monomer containing a basic nitrogen-containing part, and the balance of a unit originating from a polymerizable monomer containing a protonic neutral hydrophilic part is preferably retained on the surface of the filter material, and is preferably present in an amount of 0.6-83 mg/m$^2$ per unit volume of the filter material surface.

In specifying the amount of the polymer in the present invention, the leukocytes and platelets removing capability was evaluated under overloaded conditions rather than normal blood processing conditions. The range in which both the leukocytes removing capability and the platelet removal capability satisfy the criterion of a certain level was determined as the range for preferable amount of the polymer for simultaneous removal of leukocytes and platelets.

"To contain the polymer present on the surface of the filter material" in the present invention refers to the state of the polymer fixed to the surface of the filter material in the manner not easily eluted into the product being processed. As the method for fixing the polymer to the surface of the filter material, either a chemical method of using covalent bonding or a physical method using non-covalent bonding may be employed. If the amount of the polymer present is less than 0.6 mg/m$^2$ per unit area in the entire surface area of the filter, the leukocyte removal capability tends to decrease; if more than 83 mg/m$^2$, the platelet removal capability may decrease or the performance of the filter may fluctuate due to uneven coating. A more preferable amount of the polymer present is 5-50 mg/m$^2$ per unit area in the entire surface area of the filter, with a particularly preferable amount being 10-20 mg/m$^2$.

The amount of the polymer present on the surface of the filter material can be determined according to a common physicochemical technique. As the method for measuring the amount of the polymer present on the surface of the filter material, a method of dissolving the filter material and the polymer present on the surface in a deuteration solvent and determining the amount by nuclear magnetic resonance method (NMR, —$^1$H, —$^{13}$C) can be given.

As the method for having the polymer be present on the surface of the filter material in the present invention, known methods such as a method of fixing the above-mentioned polymerizable monomers or the polymer by chemical covalent bonding (e.g. grafting), a method of fixing by a physico-chemical non-covalent bonding (ionic bond, Van der Waals force, etc.), for example, coating, and a method of embedding the polymer can be given. More specifically, a method of directly grafting the polymerizable monomers or the polymer on the surface of the filter material by graft polymerization such as radiation grafting or plasma grafting or a method coating a polymer solution onto the filter material surface by impregnating the filter material with the polymer solution or by applying or transcribing the polymer solution to the surface of the filter material is preferable in view of a comparatively easy manufacturing process that can produce products with excellent performance in a stable manner.

Various methods can be used for coating the polymer of the present invention onto the filter material without any specific limitations inasmuch as the surface of the filter material can be coated with a certain degree of uniformity without unduly clogging the pores in the filter material. Examples of the method for coating the polymer onto the filter material include, but are not limited to, a method of impregnating the filter material with a polymer solution, a method of spraying the polymer solution to the filter material, and a method of applying or transcribing the polymer solution to the filter material using a photogravure roll or the like. Of these methods, the method of impregnating the filter material with a polymer solution and squeezing the filter material and the method of applying or transcribing the polymer solution to the filter material using a photogravure roll or the like are preferable due to the excellent continuous productivity and a low cost.

Various solvents can be used for dissolving the polymer without any specific limitations inasmuch as the solvent does not excessively dissolve the filter material. Examples of such a solvent include, but are not limited to, water and aqueous solutions containing an inorganic salt, alcohols such as methanol, ethanol, propanol, and butanol, ketones such as acetone and methyl ethyl ketone, esters such as methyl acetate and ethyl acetate, hydrocarbons such as benzene and cyclohexane, halogenated hydrocarbons such as chloroform and dichloromethane, sulfur-containing solvents such as dimethyl sulfoxide, amides such as dimethylformamide and dimethylacetamide, and mixtures of two or more of the above solvents to the extent soluble.

To dry the polymer solution after coating, a method comprising removing excess solvent by mechanical compression, by gravity, or by injecting gas such as air or nitrogen, and leaving the coated material in dry air or under reduced pressure at atmospheric temperature or with heating can be employed. To increase adhesion of the polymer of the present invention to the filter material, the surface of the filter material may be treated with a suitable agent such as an acid or alkali or may be irradiated with plasma before coating. Adhesion of the polymer to the filter material may be further increased by a heat treatment after coating with the polymer or by post processing of irradiating the coated surface with γ-rays, electron beams, or the like. The coating operation may be carried out either during manufacturing the filter material or after manufacturing the filter material.

EXAMPLES

The present invention will be explained in more detail by examples which are not intended to be limiting of the present invention.

The various numerical values in the examples and comparative examples were determined by the following methods.

Specific Surface Area of Filter Materials

The specific surface area ($m^2/g$) in the present invention refers to a value determined using Accusorb 2100 (manufactured by Shimadzu Corp.) or equivalent. After filling a sample tube with 0.50-0.55 g of the filter substrate and deaerating the tube to $1 \times 10^{-4}$ mmHg (at room temperature) for 20 hours, the specific area was determined using krypton gas as an adsorption gas at an adsorption temperature equivalent to the liquid nitrogen temperature.

Void Ratio

The void ratio in the present invention specifically exemplified for non-woven fabric is determined by calculating an apparent volume per unit gravity of the filter material ($m^3/g$) from Metsuke (weight of fabric per unit area: g/m 2) and bulk thickness (m), subtracting the solid volume per unit gravity of the filter material ($m^3/g$) from the above apparent volume ($m^3/g$), and expressing as a percentage of the apparent volume. The specific gravity of $1.35 \times 106$ ($g/m^3$) was used for the PET.

Measurement of Average Fiber Diameter

Electron microscopic photographs were taken at five points randomly selected from the surface of nonwoven fabric. A transparent sheet on which grid is drawn was layered on each photograph. The diameter of the thread at the crossing points of the grid was measured (n=100) and the average diameter was determined by converting the measured diameter using polystyrene latex of which the diameter is known as a scale.

Measurement of Average Pore Diameter

The average pore diameter was measured in PROFIL solution (manufactured by Coulter Electronics, Ltd.) using a method conforming to the airflow method described in ASTM F316-86.

Polymer Amount Per Unit Area of the Entire Surface Area of Filter

The entire surface area ($m^2$) of the filter in the present invention refers to a value obtained by multiplying the weight (g) by the specific area ($m^2/g$) of the filter.

The polymer amount ($mg/m^2$) per unit area ($m^2$) of the entire surface area of the filter of the present invention is determined by NMR analysis of a solution of a certain area (weight) of the filter dissolved in a deuteriumization solvent common to the filter material and coating agent. For example, a prescribed amount of a filter comprising a polyester nonwoven fabric coated with a polymer composition containing methyl methacrylate (MMA), dimethylaminoethyl methacrylate, and 2-hydroxyethyl methacrylate was dissolved in deuteriumized 1,1,1,3,3,3-hexafluoro-2-propanol. The ratio of intensity of the signals clearly belonging to the nonwoven fabric (e.g. proton on benzene ring) and the signals clearly belonging to the coating material (e.g. proton on the methyl group adjacent to MMA (methyl methacrylate)ester) was determined. Then, the coated amount of the polymer per unit weight of the nonwoven fabric was determined from this ratio of intensity and a separately determined copolymer composition of the coating material. The coated amount per unit weight can be converted into the coated amount per entire measured surface area of the filter.

Leukocyte Removal Performance Test Method, Pressure Test During Recovery, Scanning Electron Microscope Observation of the Filter after Filtration CPD-added fresh human whole blood was used for the blood evaluation. After being collected from a donor, the blood was stored at room temperature, the leukocyte removal performance test was carried out within about two hours after the collection. A coating solution prepared by dissolving a prescribed amount of polymer in special grade ethanol of the coating solvent was coated to a nonwoven polyester fabric (Microweb manufactured by Asahi Kasei Corporation) with a specific surface area of 1.47 $m^2/g$, void ratio of 86%, average fiber diameter of 1.2 µm, average pore diameter of 6.3 µm, and a weight of the substrate per unit area (Metsuke) of 40 $g/m^2$.

The coated material was punched into pieces with a diameter of 20 mm. 16 or 24 sheets of the nonwoven polyester fabric with a specific surface area of 1.47 $m^2/g$, void ratio of 86%, average fiber diameter of 1.2 µm, average pore diameter of 6.3 µm, and a weight per unit area of 40 $g/m^2$ were combined and fabricated into samples to be evaluated in a miniature column. The filtration area determined from the miniature column configuration was 133 $mm^2$. Blood was caused to flow at a flow rate of 0.74 ml/min using a syringe pump, and recovered a recovery amount of 6 ml or 13.3 ml.

The pressure was measured using a calibrated manometer at the end of tube branched from the miniature column inlet side tube. After filtration, the filter was washed with a physiological saline solution, fixed with glutaraldehyde, and observed the degree of erythrocyte adhesion by a known method such as a method of using scanning electron microscope.

Leukocyte/Platelet Removal Performance Test

CPD-added fresh human whole blood was used for the blood evaluation. After being collected from a donor, the blood was stored at room temperature, and the leukocyte removal performance test was carried out within about two hours after the collection. A coating solution prepared by dissolving a prescribed amount of polymer in special grade ethanol of the coating solvent was coated to a nonwoven polyester fabric ("Microweb" manufactured by Asahi Kasei Corporation) with a specific surface area of 1.47 $m^2/g$, void ratio of 86%, average fiber diameter of 1.2 µm, average pore diameter of 6.3 µm, and a weight per unit area of 40 $g/m^2$. The coated material was punched into pieces with a diameter of 20 mm. 24 sheets of the nonwoven polyester fabric with a specific surface area of 1.47 $m^2/g$, void ratio of 86%, average fiber diameter of 1.2 µm, average pore diameter of 6.3 µm, and a weight per unit area of 40 $g/m^2$ were combined and fabricated into samples to be evaluated in a miniature column. The filtration area determined from the miniature column configuration was 133 $mm^2$. Blood was caused to flow at a flow rate of 0.74 ml/min using a syringe pump, recovered a recovery amount of 13.3 ml.

Leukocyte Removal Capability

The leukocyte removal capability was calculated according to the following formula (1).

$$\text{leukocyte removal capability} = -\text{Log} \frac{\text{leukocyte concentration in recovered blood}}{\text{leukocyte concentration before filtration}} \quad (1)$$

To determine the leukocyte concentration in the blood before filtration, after staining leukocytes in the blood with a Turk solution, the blood was diluted and mixed well, then filled in a Turk counter to count the number of leukocytes in the total of 8 compartments through an optical microscope (Volume per one counting compartment=0.1 µl). On the other hand, the leukocyte concentration in the recovery solution was measured by the leukocyte counting method described in TRANSFUSION, vol. 32, NO. 6, pp 565-571 (1992). The sample preparation method (p 565) was compliant with Type B or Type C (when the leukocyte concentration was extremely small)

Platelet Removal Capability

The platelet removal capability was calculated according to the following formula (2). Platelet concentrations before and after the filtration were measured by using a multi-item automated hematology analyzer (K-4500, manufactured by Sysmex Corp.) and a flow cytometer (FACS Caliber™, manufactured by Becton Dickinson and Company). When measuring with the flow cytometer, CD 61 (manufactured by Becton Dickinson and Company), for example, was used as a platelet marker.

$$\text{Platelet removal capability} = -\text{Log} \frac{\text{Platelet concentration after filtration}}{\text{Platelet concentration before filtration}} \quad (2)$$

When the platelet concentration after filtration was too small for quantitative analysis due to inadequate precision or other reasons, inaccurate values are indicated by adding the words "over" to values with sufficient accuracy.

Eluted Substance Test of Coated Nonwoven Fabric (Examination on Total Suspended Solid)

The eluted substance test of a coated nonwoven fabric was carried out under the conditions of the sample quantity of 1 g and water quantity of 100 ml in accordance with the sterilized blood transfusion set standard (Ministerial Instruction No. 1079 under Medical Act, Dec. 11, 1998) (Standard: 1.0 mg or less).

Example 1

Polymerizable monomers were polymerized by adding an ethanol solution of the monomers and a diazo-type initiator dropwise to ethanol used as a polymerization solvent while stirring at 78° C. in nitrogen atmosphere. The charged polymerizable monomers were comprised of 3 mol % of methyl methacrylate (hereinafter referred to as "MMA"), 6 mol % of dimethylaminoethyl methacrylate (hereinafter referred to as "DM"), 91 mol % of 2-hydroxyethyl methacrylate (hereinafter referred to as "HEMA"). The polymer solution was purified using an excessive amount of water and dried under reduced pressure. The copolymerization composition of the polymer was analyzed by $^1$H-NMR. The results were almost in accord with the charged polymerizable monomer composition, with the composition of MMA, DM, and HEMA in the polymer being 3 mol %, 6 mol %, and 91 mol %, respectively (hereinafter referred to as "HAM036"). The weight average molecular weight (Mw) was 300,000. Ethanol was used as a coating solvent and the polymer concentration of 1 wt (g)/vol (ml) % (hereinafter abbreviated as "W/V %") was employed. The polymer solution with the above concentration was coated to 16 sheets of nonwoven polyester fabric with a specific surface area of 1.47 $m^2$/g, void ratio of 86%, average fiber diameter of 1.2 µm, average pore diameter of 6.3 µm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.5.

Example 2

Polymerization, purification, and drying were carried out in the same manner as in Example 1, except for using a monomer charge ratio of MMA 5 mol %, DM 6 mol %, and HEMA 89 mol %. The copolymerization composition of the polymer was analyzed by $^1$H-NMR. The monomer composition of MMA, DM, and HEMA in the copolymer was 5 mol %, 6 mol %, and 89 mol %, respectively (hereinafter referred to as "HAM056"). The weight average molecular weight (Mw) was 300,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 µm, average pore diameter of 6.3 µm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.7.

Example 3

Polymerization, purification, and drying were carried out in the same manner as in Example 1, except for using a monomer charge ratio of MMA 30 mol %, DM 6 mol %, and HEMA 64 mol %. The copolymerization composition of the polymer was analyzed by $^1$H-NMR. The monomer composition of MMA, DM, and HEMA in the copolymer was 30 mol %, 6 mol %, and 64 mol %; respectively (hereinafter referred to as "HAM306"). The weight average molecular weight (Mw) was 240,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 µm, average pore diameter of 6.3 µm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 5.4.

Example 4

Polymerization, purification, and drying were carried out in the same manner as in Example 1, except for using a monomer charge ratio of MMA 40 mol %, DM 6 mol %, and HEMA 54 mol %. The copolymerization composition of the polymer was analyzed by $^1$H-NMR. The monomer composition of MMA, DM, and HEMA in the copolymer was 40 mol %, 6 mol %, and 54 mol %, respectively (hereinafter referred to as "HAM406"). The weight average molecular weight (Mw) was 180,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.9.

Example 5

Polymerization, purification, and drying were carried out in the same manner as in Example 1, except for using a monomer charge ratio of MMA 45 mol %, DM 6 mol %, and HEMA 49 mol %. The copolymerization composition of the polymer was analyzed by $^1$H-NMR. The monomer composition of MMA, DM, and HEMA in the copolymer was 45 mol %, 6 mol %, and 49 mol %, respectively (hereinafter referred to as "HAM456"). The weight average molecular weight (Mw) was 200,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.5.

Example 6

Polymerization, purification, and drying were carried out in the same manner as in Example 1, except for using a monomer charge ratio of MMA 50 mol %, DM 6 mol %, and HEMA 44 mol %. The copolymerization composition of the polymer was analyzed by $^1$H-NMR. The monomer composition of MMA, DM, and HEMA in the copolymer was 50 mol %, 6 mol %, and 44 mol %, respectively (hereinafter referred to as "HAM506"). The weight average molecular weight (Mw) was 180,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.4.

Example 7

Polymerization, purification, and drying were carried out in the same manner as in Example 1, except for using a monomer charge ratio of MMA 60 mol %, DM 6 mol %, and HEMA 34 mol %. The copolymerization composition of the polymer was analyzed by $^1$H-NMR. The monomer composition of MMA, DM, and HEMA in the copolymer was 60 mol %, 6 mol %, and 34 mol %, respectively (hereinafter referred to as "HAM606"). The weight average molecular weight (Mw) was 220,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.0.

Comparative Example 1

Polymerization, purification, and drying were carried out in the same manner as in Example 1, except for using a monomer charge ratio of DM 6 mol % and HEMA 94 mol %. The copolymerization composition of the polymer was analyzed by $^1$H-NMR. The monomer composition of DM and HEMA in the copolymer was 6 mol % and 94 mol %, respectively (hereinafter referred to as "HAM006"). The weight average molecular weight (Mw) was 340,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 3.7.

Comparative Example 2

A miniature column was fabricated from 16 sheets of nonwoven polyester fabric without coating (abbreviation: "No coating") with a specific surface area of 1.47 $m^2$/g, void ratio of 86%, average fiber diameter of 1.2 μm, average pore diameter of 6.3 μm, and a weight per unit area of 40 g/$m^2$. A method for testing leukocyte removal performance was carried out under the conditions of a recovery amount of 6 ml to confirm that the leukocyte removal capability was 2.3.

Example 8

Polymerization, purification, and drying were carried out in the same manner as in Example 1, except for using a monomer charge ratio of MMA 30 mol %, DM 1 mol %, and HEMA 69 mol %. The copolymerization composition of the polymer was analyzed by $^1$H-NMR. The monomer composition of MMA, DM, and HEMA in the copolymer was 30 mol %, 1 mol %, and 69 mol %, respectively (hereinafter referred to as "HAM310"). The weight average molecular weight (Mw) was 250,000. The polymer solution with a concentration of 1 W/V % in ethanol used as a coating solvent was coated to 16 sheets of nonwoven polyester fabric with a specific surface area of 1.47 $m^2$/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.5.

Example 9

Polymerization, purification, and drying were carried out in the same manner as in Example 1, except for using a monomer charge ratio of MMA 30 mol %, DM 15 mol %, and HEMA 55 mol %. The copolymerization composition of the polymer was analyzed by $^1$H-NMR. The monomer composition of MMA, DM, and HEMA in the copolymer was 30 mol %, 15 mol %, and 55 mol %, respectively (hereinafter referred to as "HAM3015"). The weight average molecular weight (Mw) was 230,000. The polymer solution with a concentration of 1 W/V % in ethanol used as a coating solvent was coated to 16 sheets of nonwoven polyester fabric with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 5.1.

Example 10

Polymerization, purification, and drying were carried out in the same manner as in Example 1, except for using a monomer charge ratio of MMA 30 mol %, DM 20 mol %, and HEMA 50 mol %. The copolymerization composition of the polymer was analyzed by $^1$H-NMR. The monomer composition of MMA, DM, and HEMA in the copolymer was 30 mol %, 20 mol %, and 50 mol %, respectively (hereinafter referred to as "HAM3020"). The weight average molecular weight (Mw) was 270,000. The polymer solution with a concentration of 1 W/V % in ethanol used as a coating solvent was coated to 16 sheets of nonwoven polyester fabric with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 5.0.

Example 11

Polymerization, purification, and drying were carried out in the same manner as in Example 1, except for using a monomer charge ratio of MMA 30 mol %, DM 40 mol %, and HEMA 30 mol %. The copolymerization composition of the polymer was analyzed by $^1$H-NMR. The monomer composition of MMA, DM, and HEMA in the copolymer was 30 mol %, 40 mol %, and 30 mol %, respectively (hereinafter referred to as "HAM3040"). The weight average molecular weight (Mw) was 450,000. The polymer solution with a concentration of 1 W/V % in ethanol used as a coating solvent was coated to 16 sheets of nonwoven polyester fabric with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.6.

Example 12

Polymerization, purification, and drying were carried out in the same manner as in Example 1, except for using a monomer charge ratio of MMA 30 mol %, DM 45 mol %, and HEMA 25 mol %. The copolymerization composition of polymer was analyzed by $^1$H-NMR.

The monomer composition of MMA, DM, and HEMA in the copolymer was 30 mol %, 45 mol %, and 25 mol %, respectively (hereinafter referred to as "HAM3045"). The weight average molecular weight (Mw) was 500,000. The polymer solution with a concentration of 1 W/V % in ethanol used as a coating solvent was coated to 16 sheets of nonwoven polyester fabric with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.0.

Comparative Example 3

Polymerization, purification, and drying were carried out in the same manner as in Example 1, except for using a monomer charge ratio of MMA 30 mol % and HEMA 70 mol %. The copolymerization composition of the polymer was analyzed by $^1$H-NMR. The monomer composition of MMA and HEMA in the copolymer was 30 mol % and 70 mol %, respectively (hereinafter referred to as "HAM300"). The weight average molecular weight (Mw) was 240,000. The polymer solution with a concentration of 1 W/V % in ethanol used as a coating solvent was coated to 16 sheets of nonwoven polyester fabric with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 3.7.

Example 13

Polymerization, purification, and drying were carried out in the same manner as in Example 1, except for using a monomer charge ratio of ethyl methacrylate (hereinafter referred to as "EMA") 30 mol %, DM 6 mol %, and HEMA 64 mol %. The copolymerization composition of the polymer was analyzed by $^1$H-NMR. The monomer composition of EMA, DM, and HEMA in the copolymer was 30 mol %, 6 mol %, and 64 mol %, respectively (hereinafter referred to as "HEM306"). The weight average molecular weight (Mw) was 240,000. The polymer solution with a concentration of 1 W/V % in ethanol used as a coating solvent was coated to 16 sheets of nonwoven polyester fabric with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 4.6.

Example 14

Polymerization, purification, and drying were carried out in the same manner as in Example 1, except for using a monomer charge ratio of MMA 30 mol %, diethylaminoethyl methacrylate (hereinafter referred to as "DE") 6 mol %, and HEMA 64 mol %. The copolymerization composition of the polymer was analyzed by $^1$H-NMR. The monomer composition of MMA, DE, and HEMA in the copolymer was 30 mol %, 6 mol %, and 64 mol %, respectively (hereinafter referred to as "HAE306"). The weight average molecular weight (Mw) was 460,000. The polymer solution with a concentration of 1 W/V % in ethanol used as a coating solvent was coated to 16 sheets of nonwoven polyester fabric with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 5.0.

Example 15

Polymerization, purification, and drying were carried out in the same manner as in Example 1, except for using a monomer charge ratio of MMA 30 mol %, DM 6 mol %, and hydroxypropyl methacrylate (hereinafter referred to as "HPMA") 64 mol %. The copolymerization composition of the polymer was analyzed by $^1$H-NMR. The monomer composition of MMA, DM, and HPMA in the copolymer was 30 mol %, 6 mol %, and 64 mol %, respectively (hereinafter referred to as "PAM306"). The weight average molecular weight (Mw) was 240,000. The polymer solution with a concentration of 1 W/V % in ethanol was coated to 16 sheets of nonwoven polyester fabric with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 6 ml to confirm that the leukocyte removal capability was 5.2.

Examples 1-7 and Comparative Examples 1-2 are given to demonstrate the difference in the effect due to the absence or presence the unit originating from a hydrophobic polymerizable monomer, the absence or presence of the coating, and the proportion of copolymerized monomers. Examples 8-12 and Comparative Example 3 are given to demonstrate difference in the effect due to the absence or presence of the unit originating from a polymerizable monomer having a basic nitrogen-containing part and the composition proportion in the copolymer.

Example 13 (HEM306) is the same experiment as that of Example 3 (HAM306), except that the type of hydrophobic polymerizable monomer was changed. Example 14 (HAE306) is the same experiment as that of Example 3 (HAM306), except that the type of polymerizable monomer having a basic nitrogen-containing part was changed. Example 15 (PAM306) is the same experiment as that of Example 3 (HAM306), except that the type of polymerizable monomer having a protonic neutral hydrophilic part was changed.

The results are summarized in Table 1.

TABLE 1

|  |  | Hydrophobic (mol %) | Basic (mol %) | Hydrophilic (mol %) | Abbreviation | Leukocyte removal capability |
|---|---|---|---|---|---|---|
| Effect of the unit originating from hydrophobic monomer and copolymerization composition | Example 1 | 3 | 6 | 91 | HAM036 | 4.5 |
|  | Example 2 | 5 | 6 | 89 | HAM056 | 4.7 |
|  | Example 3 | 30 | 6 | 64 | HAM306 | 5.4 |
|  | Example 4 | 40 | 6 | 54 | HAM406 | 4.9 |
|  | Example 5 | 45 | 6 | 49 | HAM456 | 4.5 |
|  | Example 6 | 50 | 6 | 44 | HAM506 | 4.4 |
|  | Example 7 | 60 | 6 | 34 | HAM606 | 4.0 |
|  | Comparative Example 1 | 0 | 6 | 94 | HAM006 | 3.7 |
|  | Comparative Example 2 |  |  |  | No coating | 2.3 |
| Effect of the polymerizable monomer having a basic nitrogen-containing part and copolymerization composition | Example 8 | 30 | 1 | 69 | HAM301 | 4.5 |
|  | Example 9 | 30 | 15 | 55 | HAM3015 | 5.1 |
|  | Example 10 | 30 | 20 | 30 | HAM3020 | 5.0 |
|  | Example 11 | 30 | 40 | 30 | HAM3040 | 4.6 |
|  | Example 12 | 30 | 45 | 25 | HAM3045 | 4.0 |
|  | Comparative Example 3 | 30 | 0 | 70 | HAM300 | 3.7 |

TABLE 1-continued

|  |  | Hydrophobic (mol %) | Basic (mol %) | Hydrophilic (mol %) | Abbreviation | Leukocyte removal capability |
|---|---|---|---|---|---|---|
| Hydrophobic EMA | Example 13 | 30 | 6 | 64 | HEM306 | 4.6 |
| Basic DE | Example 14 | 30 | 6 | 64 | HAE306 | 5.0 |
| Hydrophilic HPMA | Example 15 | 30 | 6 | 64 | PAM306 | 5.2 |

Example 16

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by $^1$H-NMR. The monomer composition of MMA, DM, and HEMA in the copolymer was 30 mol %, 10 mol %, and 60 mol %, respectively (hereinafter referred to as "HAM3010"). The weight average molecular weight (Mw) was 230,000. The polymer solution with a concentration of 1 W/V % in ethanol used as a coating solvent was coated to 24 sheets of nonwoven polyester fabric with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.8. Pressure at the time of recovering 13.3 ml was 7.1 kPa, which was a pressure level with no problem. The filter after blood filtration was observed using a scanning electron microscope to confirm that there were almost no erythrocytes attached.

Comparative Example 4

Polymerization, purification, and drying were carried out in the same manner as in Example 1, except for using a monomer charge ratio of DM 30 mol % and HEMA 70 mol %. The copolymerization composition of the polymer was analyzed by $^1$H-NMR. The monomer composition of DM and HEMA in the copolymer was 30 mol % and 70 mol %, respectively (hereinafter referred to as "HAM030"). The weight average molecular weight (Mw) was 500,000. The polymer solution with a concentration of 1 W/V % in ethanol used as a coating solvent was coated to 24 sheets of nonwoven polyester fabric with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.8, which was almost the same as the result of Example 16. Pressure at the time of recovering 13.3 ml was 35.4 kPa, which was a very high pressure level being of a problem. The filter after blood filtration was observed using a scanning electron microscope to confirm that erythrocytes attached to cover the surface of the filter. This suggests that the erythrocytes blocked the filter pores, thereby increasing the pressure when the blood was processed at a constant flow rate.

Example 16 and Comparative Example 4 are presented to show that the degree of erythrocyte attachment confirmed by observation of the filter after filtration and the resulting pressure increase differ depending on the presence or absence of the unit originating from a hydrophobic monomer.

Blood was overloaded to the filter in Example 16 and Comparative Example 4 as compared with Examples 1-15 and Comparative Examples 1-3. Leukocyte removal capability of over 2.8 at this blood load is regarded to be highly excellent as compared with conventional filters.

Example 17

The HAM056 prepared in Example 2 was dissolved in ethanol used as a coating solvent and coated to 24 sheets of nonwoven polyester fabric of being a filter material with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.9. The platelet removal capability was 3.0 or more.

Blood is overloaded to the filter in the blood evaluation method according to this experiment. Leukocyte removal capability of over 2.8 and the platelet removal capability of over 1.6 are regarded to be highly excellent as compared with conventional filters.

Example 18

Polymerization, purification, and drying were carried out in the same manner as in Example 1, except for using a monomer charge ratio of MMA 10 mol %, DM 6 mol %, and HEMA 84 mol %. The copolymerization composition in the polymer was analyzed by $^1$H-NMR to find that the results were almost in accord with the charged polymerizable monomer composition, with the composition of MMA, DM, and HEMA in the polymer being 10 mol %, 6 mol %, and 84 mol %, respectively (hereinafter referred to as "HAM106"). The weight average molecular weight (Mw) was 310,000. The polymer solution in ethanol used as a coating solvent was coated to 24 sheets of nonwoven polyester fabric of being a filter material with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.2. The platelet removal capability was 2.9.

Example 19

Polymerization, purification, and drying were carried out in the same manner as in Example 1, except for using a monomer charge ratio of MMA 20 mol %, DM 6 mol %, and HEMA 74 mol %. The copolymerization composition in the polymer was analyzed by $^1$H-NMR to find that the results were almost in accord with the charged polymerizable monomer composition, with the composition of MMA, DM, and HEMA in the polymer being 20 mol %, 6 mol %, and 74 mol %, respectively (hereinafter referred to as "HAM206"). The weight average molecular weight (Mw) was 330,000. The polymer solution in ethanol used as a coating solvent was coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.5. The platelet removal capability was 2.3.

Example 20

The HAM306 prepared in Example 3 was dissolved in ethanol used as a coating solvent and coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 4.0. The platelet removal capability was 3.0 or more.

Example 21

The HAM406 prepared in Example 4 was dissolved in ethanol used as a coating solvent and was coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.1. The platelet removal capability was 3.0 or more.

Example 22

The HAM456 prepared in Example 5 was dissolved in ethanol used as a coating solvent and was coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.8. The platelet removal capability was 3.0 or more.

Comparative Example 5

The HAM006 prepared in Comparative Example 1 was dissolved in ethanol used as a coating solvent and was coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.5. The platelet removal capability was 0.5.

Reference Example 1

In this Reference Example shown below, blood was overloaded to the filter to show that the polymer composition and the amount of polymer in the filter are preferably in specific ranges for the filter to exhibit high removal capability of both leukocytes and platelets.

Therefore, this Reference Example does not deny at all the excellent leukocyte removal capability of the filter having the polymer composition and the amount of polymer outside of those specific ranges over conventional filters in a normal blood throughput operation.

In the following description, examples showing the polymer composition and the amount of the polymer in the filter material outside of the specific ranges which satisfy high requirement for leukocyte removal capability and platelet removal capability are regarded as reference examples.

The HAM506 prepared in Example 6 was dissolved in special grade ethanol used as a coating solvent and was coated to 24 sheets of nonwoven polyester fabric of being a filter material with a specific surface area of 1.47 $m^2$/g, void ratio of 86%, average fiber diameter of 1.2 μm, average pore diameter of 6.3 μm, and a weight per unit area of 40 g/$m^2$. The coated amount was 12 mg/$m^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.0. The platelet removal capability was 3.0 or more.

Example 23

The HAM301 prepared in Example 8 was dissolved in ethanol used as a coating solvent and was coated to 24 sheets of nonwoven polyester fabric of being a filter material with a specific surface area of 1.47 m²/g, void ratio of 86%, average fiber diameter of 1.2 m, average pore diameter of 6.3 µm, and a weight per unit area of 40 g/m². The coated amount was 12.5 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.3. The platelet removal capability was 1.7.

Example 24

Polymerization, purification, and drying were carried out in the same manner as in Example 1, except for using a monomer charge ratio of MMA 30 mol %, DM 3 mol %, and HEMA 67 mol %. The copolymerization composition in the polymer was analyzed by ¹H-NMR to find that the results were almost in accord with the charged polymerizable monomer composition, with the composition of MMA, DM, and HEMA in the polymer being 30 mol %, 3 mol %, and 67 mol %, respectively (hereinafter referred to as "HAM303"). The weight average molecular weight (Mw) was 260,000. The polymer solution in special grade ethanol used as the coating solvent was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m. The coated amount was 12.5 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.3. The platelet removal capability was 1.8.

Example 25

The HAM3010 prepared in Example 16 was dissolved in ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.8. The platelet removal capability was 3.0 or more.

Example 26

The HAM3015 prepared in Example 9 was dissolved in ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.5. The platelet removal capability was 3.0 or more.

Comparative Example 6

The HAM300 prepared in Comparative Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.5. The platelet removal capability was 0.9.

Reference Example 2

The HAM3020 prepared in Example 10 was dissolved in special grade ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 1.2. The platelet removal capability was 2.8.

Although the leukocyte removal capability unduly decreased, observation of the filter after blood filtration by a scanning electron microscope confirmed that there were almost no erythrocytes attached.

Example 27

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 0.8 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.8. The platelet removal capability was 2.7.

Example 28

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 µm, average pore diameter of 6.3 µm, and a weight per unit area of 40 g/m². The coated amount was 6 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.8. The platelet removal capability was 2.6.

Example 29

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 8 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.9. The platelet removal capability was 2.6.

Example 30

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 m, average pore diameter of 6.3 μm, and a weight per unit area of 40 g/m². The coated amount was 18 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.3. The platelet removal capability was 2.4.

Example 31

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 50 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.1. The platelet removal capability was 1.9.

Example 32

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 80 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.8. The platelet removal capability was 1.6.

Reference Example 3

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 0.5 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 1.5. The platelet removal capability was 2.7.

Reference Example 4

The HAM306 prepared in Example 3 was dissolved in ethanol used as a coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 85 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 2.5. The platelet removal capability was 1.3.

Example 33

Polymerization, purification, and drying were carried out in the same manner as in Example 1, except for using a monomer charge ratio of EMA 20 mol %, DM 6 mol %, and HEMA 74 mol %. The copolymerization composition in the polymer was analyzed by $^1$H-NMR to find that the results were almost in accord with the charged polymerizable monomer composition, with the composition of EMA, DM, and HEMA in the polymer being 20 mol %, 6 mol %, and 74 mol %, respectively (hereinafter referred to as "HEM206"). The weight average molecular weight (Mw) was 240,000. The polymer solution in special grade ethanol used as the coating solvent and was coated to 24 sheets of nonwoven polyester fabric of being a filter material with a specific surface area of 1.47 m²/g, void ratio of 86%, average fiber diameter of 1.2 μm, average pore diameter of 6.3 μm, and a weight per unit area of 40 g/m². The coated amount was 12 mg/m² per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.0. The platelet removal capability was 3.0 or more.

Example 34

The HAE306 prepared in Example 14 was dissolved in ethanol used as a coating solvent and was coated to 24 sheets of nonwoven polyester fabric of being a filter material with a specific surface area of 1.47 m$^2$/g, void ratio of 86%, average fiber diameter of 1.2 μm, average pore diameter of 6.3 m, and a weight per unit area of 40 g/m$^2$. The coated amount was 12 mg/m$^2$ per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.4. The platelet removal capability was 3.0 or more.

Example 35

The PAM306 prepared in Example 15 was dissolved in ethanol used as a coating solvent and was coated to 24 sheets of nonwoven polyester fabric of being a filter material with a specific surface area of 1.47 m$^2$/g, void ratio of 86%, average fiber diameter of 1.2 μm, average pore diameter of 6.3 μm, and a weight per unit area of 40 g/m$^2$. The coated amount was 12 mg/m per unit area on the entire surface area of the filter. Evaporation residue was measured and found to be not more than 0.1 mg. A miniature column was fabricated from the above nonwoven fabric. A method for testing leukocyte removal performance was carried out under the conditions of a recovery amount of 13.3 ml to confirm that the leukocyte removal capability was 3.6. The platelet removal capability was 3.0 or more.

Examples 17-22, Comparative Example 5, and Reference Example 1 are given to show the difference in the effect due to the proportion of the unit originating from a hydrophobic polymerizable monomer in the copolymer. Examples 23 and 24, Comparative Example 6, and Reference Example 2 are given to demonstrate difference in the effect due to the proportion of the unit originating from a polymerizable monomer having a basic nitrogen-containing part in the copolymer.

Examples 27-32 and Comparative Examples 3 and 4 are given to show the difference in the effect due to the amount of polymer.

Example 33 (HEM206) is the same experiment as that of Example 19 (HAM206), except that the type of hydrophobic polymerizable monomer was changed. Example 34 (HAE306) is the same experiment as that of Example 20 (HAM306), except that the type of polymerizable monomer having a basic nitrogen-containing part was changed. Example 35 (PAM306) is the same experiment as that of Example 20 (HAM306), except that the type of polymerizable monomer having a protonic neutral hydrophilic part was changed.

TABLE 2

| | | Hydrophobic (mol %) | Basic (mol %) | Hydrophilic (mol %) | Abbreviation | Coated amount (mg/m$^2$) | Leukocyte removal capability | Platelet removal capability |
|---|---|---|---|---|---|---|---|---|
| Effect of the unit originating from hydrophobic monomer and copolymerization composition | Example 17 | 5 | 6 | 89 | HAM056 | 12 | 2.9 | Over 3.0 |
| | Example 18 | 10 | 6 | 84 | HAM106 | 12 | 3.2 | 2.9 |
| | Example 19 | 20 | 6 | 74 | HAM206 | 12 | 3.5 | 2.3 |
| | Example 20 | 30 | 6 | 64 | HAM306 | 12 | 4.0 | Over 3.0 |
| | Example 21 | 40 | 6 | 54 | HAM406 | 12 | 3.1 | Over 3.0 |
| | Example 22 | 45 | 6 | 49 | HAM456 | 12 | 2.8 | Over 3.0 |
| | Comparative Example 5 | 0 | 6 | 94 | HAM006 | 12 | 2.5 | 0.5 |
| | Reference Example 1 | 50 | 6 | 44 | HAM506 | 12 | 2.0 | Over 3.0 |
| Effect of the polymerizable monomer having a basic nitrogen-containing part and copolymerization composition | Example 23 | 30 | 1 | 69 | HAM301 | 12.5 | 3.3 | 1.7 |
| | Example 24 | 30 | 3 | 67 | HAM303 | 12.5 | 3.3 | 1.8 |
| | Example 25 | 30 | 10 | 60 | HAM3010 | 12 | 3.8 | Over 3.0 |
| | Example 26 | 30 | 15 | 55 | HAM3015 | 12 | 3.5 | Over 3.0 |
| | Comparative Example 6 | 30 | 0 | 70 | HAM300 | 12 | 2.5 | 0.9 |
| | Reference Example 2 | 30 | 20 | 50 | HAM3020 | 12 | 1.2 | 2.8 |
| Effect of the amount | Example 27 | 30 | 6 | 64 | HAM306 | 0.8 | 2.8 | 2.7 |
| | Example 28 | 30 | 6 | 64 | HAM306 | 6 | 2.8 | 2.6 |
| | Example 29 | 30 | 6 | 64 | HAM306 | 8 | 2.9 | 2.6 |
| | Example 30 | 30 | 6 | 64 | HAM306 | 18 | 3.3 | 2.4 |
| | Example 31 | 30 | 6 | 64 | HAM306 | 50 | 3.1 | 1.9 |
| | Example 32 | 30 | 6 | 64 | HAM306 | 80 | 2.8 | 1.6 |
| | Reference Example 3 | 30 | 6 | 64 | HAM306 | 0.5 | 1.5 | 2.7 |
| | Reference Example 4 | 30 | 6 | 64 | HAM306 | 85 | 2.5 | 1.3 |
| Hydrophobic EMA | Example 33 | 20 | 6 | 74 | HEM206 | 12 | 3.0 | Over 3.0 |
| Basic DE | Example 34 | 30 | 6 | 64 | HAE306 | 12 | 3.4 | Over 3.0 |
| Hydrophilic HPMA | Example 35 | 30 | 6 | 64 | PAM306 | 12 | 3.6 | Over 3.0 |

INDUSTRIAL APPLICABILITY

As described above, the polymer of the present invention formed from a unit originating from a hydrophobic polymerizable monomer, a unit originating from a polymerizable monomer containing a basic nitrogen-containing part, and a unit originating from a polymerizable monomer containing a protonic neutral hydrophilic part was found to be able to suppress a mutual action with erythrocytes while maintaining high leukocyte affinity.

In addition, if a blood product containing leukocytes is filtered through the leukocyte removal filter containing the above polymer on at least a part of the surface, the surface can be provided with increased affinity to leukocytes which cause a blood transfusion side effect as compared with erythrocytes which is useful cells in the blood. As a result, the leukocyte removal capability per unit area can increased and the filter apparatus volume can be downsized, whereby a loss of useful components remaining in the filter can be reduced. A leukocyte removing filter which does not exhibit an increase in the process time during an operation with a head difference and a pressure increase at a constant flow rate due to attachment of erythrocytes can be provided.

In addition, a filter possessing both the leukocyte removal capability and platelet removal capability can be provided by using the filter containing the polymer formed from a unit originating from a hydrophobic polymerizable monomer, a unit originating from a polymerizable monomer containing a basic nitrogen-containing functional group part, and a unit originating from a polymerizable monomer containing a protonic neutral hydrophilic part, in a specific proportion and in a specific amount on the surface.

The invention claimed is:

1. A filter for removing leukocytes and platelets, said filter having a polymer consisting of:
    5-45 mol % of a unit originating from a hydrophobic polymerizable monomer selected from the group consisting of: methyl acrylate, methyl methacrylate, ethyl acrylate, ethyl methacrylate, butyl acrylate, butyl methacrylate, phenyl acrylate, phenyl methacrylate, ethylhexyl acrylate, ethylhexyl methacrylate, trichloroethyl acrylate, and trichloroethyl methacrylate;
    1-15 mol % of a unit originating from a polymerizable monomer containing a basic nitrogen-containing part, wherein said polymerizable monomer is selected from the group consisting of: dimethylaminoethyl acrylate, dimethylaminoethyl methacrylate, diethylaminoethyl acrylate, diethylaminoethyl methacrylate, 3-dimethylamino-2-hydroxypropyl acrylate, and 3-dimethylamino-2-hydroxy propyl methacrylate; and
    the balance of a unit originating from a polymerizable monomer containing a protonic neutral hydrophilic part, wherein said polymerizable monomer is 2-hydroxyethyl methacrylate or hydroxypropyl methacrylate,
    wherein the filter has an average pore diameter of 1-60 µm, and
    said polymer is present on the entire surface of the filter in an amount of 5-50 mg/m$^2$ per unit area of the filter surface.

2. The filter for removing leukocytes and platelets according to claim 1, wherein the polymer is a vinyl polymer.

3. The filter for removing leukocytes and platelets according to claim 1, wherein the basic nitrogen-containing part is a tertiary amino group.

4. The filter for removing leukocytes and platelets according to claim 1, wherein the protonic neutral hydrophilic part is a hydroxyl group.

5. The filter for removing leukocytes and platelets according to claim 1, wherein the filter material is a fibrous medium or a sponge-like structural material.

6. The filter for removing leukocytes and platelets according to claim 5, wherein the filter material is a nonwoven fabric.

7. The filter for removing leukocytes and platelets according to claim 5, wherein,
    the filter material has a specific surface area of 1.0 m$^2$/g or more and a void ratio of 70% or more,
    the average fiber diameter is 0.3-3.0 µm, and
    the filling density is 0.1-0.5 g/cm$^3$.

* * * * *